United States Patent
Lee et al.

(10) Patent No.: US 12,196,767 B2
(45) Date of Patent: Jan. 14, 2025

(54) METHOD FOR DETECTING VITAMIN D IN BLOOD BY USING LDI-MS, AND DEVICE FOR SAME

(71) Applicant: KOREA RESEARCH INSTITUTE OF STANDARDS AND SCIENCE, Daejeon (KR)

(72) Inventors: Tae Geol Lee, Daejeon (KR); Jin Gyeong Son, Daejeon (KR); Sunho Joh, Daejeon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 397 days.

(21) Appl. No.: 17/637,302

(22) PCT Filed: Nov. 11, 2019

(86) PCT No.: PCT/KR2019/015276
§ 371 (c)(1),
(2) Date: Feb. 22, 2022

(87) PCT Pub. No.: WO2021/033836
PCT Pub. Date: Feb. 25, 2021

(65) Prior Publication Data
US 2022/0283189 A1 Sep. 8, 2022

(30) Foreign Application Priority Data
Aug. 22, 2019 (KR) .................. 10-2019-0103035

(51) Int. Cl.
*H01J 49/04* (2006.01)
*G01N 21/31* (2006.01)
(Continued)

(52) U.S. Cl.
CPC ............. *G01N 33/82* (2013.01); *G01N 21/31* (2013.01); *G01N 30/72* (2013.01);
(Continued)

(58) Field of Classification Search
None
See application file for complete search history.

(56) References Cited

U.S. PATENT DOCUMENTS

| 2013/0186186 A1 | 7/2013 | Calton et al. |
| 2018/0127873 A1* | 5/2018 | Sarnet ............... C23C 16/45536 |
| 2019/0270113 A1* | 9/2019 | Pope ....................... B29C 41/08 |

FOREIGN PATENT DOCUMENTS

| CN | 105823782 A | 8/2016 |
| JP | 2008513781 A | 5/2008 |

(Continued)

OTHER PUBLICATIONS

Kim et al., A layer-by-layer assembled MoS2 thin film as an efficient platform for laser desorption/ionization mass spectrometry analysis of small molecules; Nanoscale, 2017, 9, 10854-10860 (Year: 2017).*

(Continued)

*Primary Examiner* — Eliza W Osenbaugh-Stewart
(74) *Attorney, Agent, or Firm* — Hauptman Ham, LLP (57) ABSTRACT

A method of detecting vitamin D in blood using laser desorption/ionization mass spectrometry (LDI-MS) and an apparatus therefor according to the present invention are not complicated in a measurement, do not require a number of measurement steps, and allow for easy measurement and collection of results in real time with a quick analysis. In addition, precise analysis may be performed even at a lower concentration of a sample, such that sensitivity and precision are excellent, various subtypes of vitamin D may be simultaneously detected, a throughput is high, and structural analysis and quantitative analysis of vitamin D that has undergone a metabolic process in blood may be accurately performed without a matrix interference.

10 Claims, 7 Drawing Sheets

(51) Int. Cl.
G01N 30/72 (2006.01)
G01N 33/82 (2006.01)

(52) U.S. Cl.
CPC ...... H01J 49/0418 (2013.01); H01J 49/0431 (2013.01); *G01N 2560/00* (2013.01)

(56) References Cited

FOREIGN PATENT DOCUMENTS

| JP | 2014520265 A | 8/2014 |
|---|---|---|
| KR | 20180068280 A | 6/2018 |
| KR | 20180104080 A | 9/2018 |
| KR | 20180131016 A | 12/2018 |

OTHER PUBLICATIONS

International Search Report issued in corresponding International Application No. PCT/KR2019/015276, dated May 21, 2020, pp. 1-4, Korean Intellectual Property Office, Daejeon, Republic of Korea.
Chang et al., "Analyses of functional polymer-modified nanoparticles for protein sensing by surface-assisted laser desorption/ionization mass spectrometry coupled with HgTe nanomatrices," Colloids and Surfaces B: Biointerfaces, vol. 130 (2015), pp. 157-163.
Japanese Office Action issued in corresponding Japanese Application No. 2022-512330, dated Jan. 18, 2023, pp. 1-7.

\* cited by examiner

METHOD FOR DETECTING VITAMIN D IN BLOOD BY USING LDI-MS, AND DEVICE FOR SAME

RELATED APPLICATIONS

The present application is a U.S. National Phase of International Application Number PCT/KR2019/015276, filed Nov. 11, 2019, and claims priority to Korean Application No. 10-2019-0103035, filed Aug. 22, 2019, the entireties of which are hereby incorporated herein.

TECHNICAL FIELD

The following disclosure relates to a method of detecting vitamin D in blood and an apparatus for detecting vitamin D in blood.

BACKGROUND

Vitamin D is an essential nutrient for maintenance of calcium homeostasis and metabolism of bones and minerals. When vitamin D is deficient, a risk of osteoporosis and fractures is increased, which may lead to rickets and the like in children and osteomalacia and the like in adults. As a result of recent studies, it has been reported that a lack of vitamin D is related to not only metabolism of bones, but also the occurrence of diabetes, cancers, cardiovascular diseases, autoimmune diseases, and the like. For example, vitamin D is required to produce antibacterial peptides such as cathelicidin, and is also required to eradicate pathogens such as *Mycobacterium tuberculosis* in human macrophages. Vitamin D exists in the body in two forms of vitamin $D_2$ and vitamin $D_3$. Vitamin $D_2$ is mainly synthesized in plants, and vitamin $D_3$ is mainly synthesized in the skin when exposed to ultraviolet rays. In the body, vitamin D is bound to a binding protein, is transported to the liver, and is hydroxylated to 25-hydroxyvitamin D (25(OH)D). This substance is a marker that best reflects the state of vitamin D in the body, and becomes 1α,25-dihydroxyvitamin D [1α,25 (OH)$_2$D], which is active in the kidneys. A concentration of vitamin D in blood in humans is affected by lifestyle such as clothing and sunlight exposure, intake of vitamin D-fortified foods, season, environments, and the like. Currently, as a clinical method for quantifying 25(OH)D, liquid chromatography tandem mass spectrometry (LC-MS/MS), high-performance liquid chromatography mass spectrometry (HPLC-MS), a competitive immunoassay (a radioimmuno assay (RIA) or the like), and an enzyme-linked immunosorbent assay (ELISA) are mainly used. In clinical laboratories, quantification of vitamins in a patient sample is performed using liquid chromatography tandem mass spectrometry is used; however, it is difficult to measure in real time because it takes 3 to 5 minutes for each sample to be analyzed, and it is not easy to immediately collect measured data. In addition, it is difficult to analyze a large number of samples, and there is a limitation in complexity because a number of experimental steps are required.

Therefore, it is required to quickly collect results of vitamin D from clinical samples, and there is a need for intensive studies on a method of detecting vitamin D in blood that may implement direct and high-throughput detection as well as an improvement in accuracy and sensitivity, and an apparatus therefor, in order to confirm disease diagnosis and drug treatment response.

RELATED ART DOCUMENT

Patent Document (Patent Document 1) KR10-2018-0068280 A (Jun. 21, 2018)

SUMMARY

An embodiment of the present invention is directed to providing a method of detecting vitamin D in blood using laser desorption/ionization mass spectrometry (LDI-MS) that is not complicated in a measurement, does not require a number of measurement steps, and allows for easy measurement and collection of results in real time with a quick analysis, and an apparatus therefor.

Another embodiment of the present invention is directed to providing a method of detecting vitamin D in blood using LDI-MS that is excellent in sensitivity and precision due to precise analysis at a lower concentration of a sample, enables precise detection of various subtypes of vitamin D, has a high-throughput, and may accurately perform structural analysis of vitamin D in blood and quantitative analysis thereof without a matrix interference, and an apparatus therefor.

In one general aspect, a method of detecting vitamin D in blood using laser desorption/ionization mass spectrometry (LDI-MS) includes: a sample loading step of loading a sample containing blood on a tungsten ditelluride layer of an LDI-MS sample loading array including a substrate layer and the tungsten ditelluride layer stacked on the substrate layer; and an analysis step of analyzing the sample loaded on the LDI-MS sample loading array by LDI-MS to detect vitamin D in the sample.

The analysis step may include a quantification step of calculating a content of the vitamin D.

The analysis step may include: a step of acquiring an LDI-MS spectrum; a step of deriving a calibration curve using the spectrum; a step of checking the calibration curve; and a step of quantitatively analyzing the sample using the calibration curve.

The method may further include, before the sample loading step, a step of adding an internal standard to a liquid sample, wherein the quantification step may include a step of determining a content of the vitamin D from a peak intensity corresponding to the vitamin D and a peak intensity corresponding to the internal standard in the LDI-MS spectrum.

The quantification step may include a step of acquiring a corrected spectrum, and a coefficient of determination in the corrected spectrum may be 0.9 or more.

In another general aspect, an LDI-MS sample loading array for detecting vitamin D in blood includes: a substrate layer; and a tungsten ditelluride layer stacked on the substrate layer and is provided to load a sample containing blood.

The tungsten ditelluride layer may include a plurality of tungsten ditelluride nanoflake particles in contact with the substrate layer.

An average thickness of the tungsten ditelluride nanoflake particles may be 2 to 15 nm.

The tungsten ditelluride nanoflake particles in the tungsten ditelluride layer may be present in an amount of 0.0001 to 100 mg/cm$^2$ per unit area.

The tungsten ditelluride layer may be produced by spotting a solution in which tungsten ditelluride nanoflake particles are dispersed on the substrate layer and then evaporating a dispersion medium.

The tungsten ditelluride nanoflake particles in the solution may be included in an amount of 0.001 to 10 wt %.

The solution may be spotted in the same region in an amount of 0.001 to 100 μl (25° C., 1 atm) two times or more.

An average thickness of the tungsten ditelluride layer may be 0.001 to 500 μm.

The substrate layer may include one or two or more selected from aluminum, copper, iron, nickel, zinc, chromium, silver, and silicon ($SiO_2$).

The sample loading array may be used for qualitative or quantitative analysis of vitamin D present in blood.

In still another general aspect, an LDI-MS sample loading kit includes the LDI-MS sample loading array for detecting vitamin D in blood.

In further still another general aspect, a laser desorption/ionization mass spectrometer includes the LDI-MS sample loading array for detecting vitamin D in blood.

Other features and aspects will be apparent from the following detailed description, the drawings, and the claims.

DETAILED DESCRIPTION OF EMBODIMENTS

Hereinafter, a method of detecting vitamin D in blood using laser desorption/ionization mass spectrometry (LDI-MS) and an apparatus therefor according to the present invention will be described in detail with reference to the accompanying drawings.

The drawings described in the present specification are provided by way of example so that the spirit of the present invention can be sufficiently transferred to those skilled in the art. Therefore, the present invention is not limited to the drawings suggested, and may be implemented in other forms. In addition, the drawings may be exaggerated in order to clear the spirit of the present invention.

Unless otherwise defined, all the technical terms and scientific terms used in the present specification have the same meanings as commonly understood by those skilled in the art to which the present invention pertains. The description for the known function and configuration unnecessarily obscuring the gist of the present invention will be omitted in the following description and the accompanying drawings.

Unless the context clearly indicates otherwise, the singular forms of the terms used in the present specification may be interpreted as including the plural forms.

Unless otherwise defined, a unit of "%" used in the present specification unless specifically mentioned refers to "wt %".

The term "layer" or "film" mentioned in the present specification means that each material forms a continuum and has a dimension having a small thickness relative to a width and a length. Accordingly, in the present specification, the term "layer" or "film" should not be interpreted as a two-dimensional flat plane.

The present invention provides a method of detecting vitamin D in blood using LDI-MS, an LDI-MS sample loading array for detecting vitamin D in blood, an LDI-MS sample loading kit including the array, and a laser desorption/ionization mass spectrometer including the array. In the present specification, LDI-MS is the abbreviation for laser desorption/ionization mass spectrometry.

In the present invention, tungsten ditelluride ($WTe_2$) is used, such that the precision of quantitative analysis of vitamin D is remarkably excellent compared with molybdenum disulfide ($MoS_2$) and the like. A chip-based LDI-MS array is used using uniformly deposited tungsten ditelluride ($WTe_2$) nanoflake particles, such that a simple platform for high-throughput analysis may be provided, and an analysis time may be significantly reduced because sample preparation may be partially or fully automated. In addition, accuracy and precision in mass spectrometry may be significantly improved. Therefore, unlike the case of LC-MS/MS in which steps are complicated and real-time detection is practically difficult, in the present invention, real-time detection and analysis of vitamin D may be implemented, and the precision of qualitative and quantitative analysis is more excellent.

In the chromatography-type spectrometry according to the related art, since a peak that appears at a specific time is analyzed, only one type of target analyte may be analyzed, and it is difficult to perform simultaneous multi-component analysis. On the other hand, in the present invention using LDI-MS, since an analyst may simultaneously measure molecules present in a sample in a time-of-flight type, multi-component analysis may be quickly performed. In addition, in the existing chromatography-type spectrometry, it takes a certain time for a liquid sample to pass through a chromatography tube, and thus, several minutes per sample are required. On the other hand, in the present invention using LDI-MS, since a simple method such as a method of introducing a plate placed and dried on the sample loading array and performing analysis with a laser is used, signals may be obtained within seconds, and thus, the analysis may be quickly performed.

The blood is preferably serum or a serum extract separated through centrifugation or the like. The serum extract may be obtained from serum by various extraction methods such as liquid-liquid extraction (LLE) and solid phase extraction (SPE). It is preferable to use serum or a serum extract in terms of preventing a decrease in precision of quantification of vitamins due to a matrix effect caused by red blood cells, white blood cells, platelets, and the like. That is, in a case where the spectrometry or apparatus according to the present invention is used for serum or a serum extract, very precise quantitative analysis may be performed.

According to the present invention, a method of detecting vitamin D in blood using LDI-MS includes: a sample loading step of loading a sample containing blood on a tungsten ditelluride layer of an LDI-MS sample loading array including a substrate layer and the tungsten ditelluride layer stacked on the substrate layer; and an analysis step of analyzing the sample loaded on the LDI-MS sample loading array by LDI-MS to detect vitamin D in the sample.

The term "sample" used in the present specification refers to blood or a sample containing blood. As the blood, blood itself may be used, or plasma separated from blood may be used.

In the analysis step, a known means for analysis using LDI-MS, such as qualitative analysis or quantitative analysis, may be used. For example, the analysis step may include: a step of acquiring an LDI-MS spectrum; a step of deriving a calibration curve using the spectrum; a step of checking/analyzing the calibration curve; and/or a step of quantitatively analyzing the sample using the calibration curve. The complexity of the obtained spectrum is determined by the influence of the matrix in the sample. Examples of components of the matrix that increase the complexity of the spectrum include proteins, lipids, and low-molecular metabolites present in plasma, and a trace amount of several ions. Therefore, a clean spectrum may be obtained in the analysis region through a pretreatment for removing materials that may inhibit ionization of an analyte, such as proteins and lipids. However, in a case where the sensitivity of the apparatus is decreased even though a suitable pretreatment is performed, different intensities of the signals may be detected. Therefore, the value may be corrected using D3-25OH-vitamin $D_3$ that is an internal standard of 25OH-vitamin $D_3$-$d_3$ ($^2$H). In addition, a material that helps ionization may be derivatized into an assay material depending on an ionization method, and for example, Amplifex kit may be used.

An m/z region of the mass spectrometer used in LDI-MS may refer to a known document used in LDI-MS, and may be, for example, 100 to 2,000 da. In this range, ions derivatized with 25OH-vitamin $D_3$ may be directly detected, and quantitative analysis may be performed from the amount of ions detected. In addition, since the intensity of the laser in LDI-MS may increase the complexity of the spectrum by the ionization due to the underlying material causing ionization, it is preferable to adjust the intensity of the laser to an appropriate intensity.

In an exemplary embodiment of the present invention, the analysis step may include a quantification step of calculating a content of the vitamin D. Examples of the quantification step include a quantification step using an internal standard.

That is, the method of detecting vitamin D in blood using LDI-MS may further include, before the sample loading step, a step of adding an internal standard to a liquid sample. The quantification step may include a step of determining a content of the vitamin D from a peak intensity corresponding to the vitamin D and a peak intensity corresponding to the internal standard in the LDI-MS spectrum. Any internal standard may be used as long as it may be distinguished from vitamin D in the analysis step and has physicochemical properties (ionization properties and solubility) similar to those of vitamin D. Precise quantitative analysis of vitamin D may be performed by a molecular weight difference using the internal standard.

In an exemplary embodiment of the present invention, the quantification step may include a step of acquiring a corrected spectrum, and a coefficient of determination in the corrected spectrum may be 0.9 or more, specifically 0.93 or more, and more specifically 0.95 or more. That is, in the present invention, the precision of the quantitative analysis is significantly excellent. In this case, it is sufficient that an upper limit is 1 or less.

In the method of detecting vitamin D in blood using LDI-MS according to an exemplary embodiment of the present invention, a limit of detection (LoD) may be 0.01 pmol/µl (target molecule/blood) or less. That is, in the present invention, even when a trace amount of blood is used, the precise quantitative analysis may be performed.

According to the present invention, an LDI-MS sample loading array for detecting vitamin D in blood includes: a substrate layer; and a tungsten ditelluride layer stacked on the substrate layer and is provided to load a sample containing blood.

In an exemplary embodiment of the present invention, the tungsten ditelluride layer may include a plurality of tungsten ditelluride nanoflake particles in contact with the substrate layer.

The tungsten ditelluride nanoflake particle has at least one of a nano-sized short width, long width, and thickness, and has a plate shape. The tungsten ditelluride nanoflake particles may be produced by various methods. For example, a method of producing tungsten ditelluride nanoflake particles by mechanically or chemically peeling a single or multi-layered two-dimensional material from a single crystal mass, specifically, a peeling method using a phenomenon in which a rapid reaction between water and lithium occurs by immersing a transition metal dichalcogenide (TMD) single crystal mass in a solution containing lithium ions so that the lithium ions are intercalated, and then exposing them to water, a deposition method for synthesizing a TMD material on a substrate (chemical vapor deposition method or the like), and the like may be used. In addition, any method may be used as long as nano-sized plate-shaped tungsten ditelluride nanoflake particles may be produced.

Specific examples of the standard of the tungsten ditelluride nanoflake particle are as follows, but are merely described as preferred examples, and the present invention is not necessarily limited thereto. As a preferred example, the tungsten ditelluride nanoflake particles may have an average thickness of 0.8 to 50 nm, specifically 0.8 to 15 nm, and more specifically 0.8 to 5 nm, may have an average long width of 1 to 5,000 nm, and may be present on the substrate layer in an amount of 0.0001 to 100 mg/cm$^2$ per unit area. In addition, a surface roughness of the tungsten ditelluride layer may be 1 to 500 nm.

The tungsten ditelluride layer may be produced by spotting a dispersion in which tungsten ditelluride nanoflake particles are dispersed on the substrate layer and then evaporating the dispersion. In this case, in the dispersion, various solvents such as water, a polar organic solvent, a non-polar organic solvent, and a bipolar organic solvent may be selected depending on a degree of hydrophobicity of a surface of the substrate layer. A hydrophobic solvent, that is, a non-polar solvent, is preferably used so that the solvent does not spread too much on the surface of the substrate layer and the tungsten ditelluride nanoflake particles to be loaded on the hydrophobic surface of the substrate layer are controlled to have an appropriate shape and structure. In this case, the non-polar solvent is preferable to have higher hydrophobicity. Examples of the non-polar solvent include alcohols having C3-C6 carbon atoms, such as isopropanol, n-propanol, butanol, pentanol, and hexanol; polyhydric alcohols such as ethylene glycol and propylene glycol; and cyclic compounds such as benzene, toluene, and hexane, and among them, isopropanol is more preferred.

In this case, a dispersion medium is preferable to have higher hydrophobicity so that the tungsten ditelluride nanoflake particles have an appropriate shape and structure. Examples of the non-polar solvent include alcohols having C3-C6 carbon atoms, such as isopropanol, n-propanol, butanol, pentanol, and hexanol; polyhydric alcohols such as ethylene glycol and propylene glycol; and cyclic compounds such as benzene, toluene, and hexane, and among them, isopropanol is more preferred. The property of the surface of the substrate layer is preferably hydrophobic so that the tungsten ditelluride nanoflake particles in the tungsten ditelluride layer are loaded on the substrate layer into an appropriate size without spread on the surface after being spotted on the substrate layer from the dispersion in which the tungsten ditelluride nanoflake particles are dispersed. In the case where the tungsten ditelluride layer including the tungsten ditelluride nanoflake particles is formed on the substrate layer by spotting and drying the dispersion containing the dispersion medium, it is possible to maintain a distributed loading state of a regular pattern with a more stable structure, and more precise qualitative and quantitative analysis may be performed.

The substrate layer may have a hydrophobic surface. As an example, a material including one or two or more selected from aluminum, copper, iron, nickel, zinc, chromium, silver, and silicon ($SiO_2$) may be used for the substrate layer. As a specific example, a stainless steel substrate layer or a silicon substrate layer is more preferably used. In addition, another substrate layer coated with a coating layer having a hydrophobic surface may also be used. As a specific example, a substrate layer coated with a thin film formed of a hydrophobic organic material such as trichloro(1H,1H,2H,2H-perfluorooctyl)silane or a self-assembled monolayer (SAM) may be used, and a hydrophobic nanostructure may be formed on the surface of the substrate layer. However, this is only described as a specific example, and the present invention is not necessarily limited thereto.

A composition ratio of the dispersion is not particularly limited because it may be adjusted so that the tungsten ditelluride nanoflake particles are finally dispersed on the substrate layer and are present in a loaded state in an appropriate amount. For example, the tungsten ditelluride nanoflake particles in the dispersion may be included in an amount of 0.001 to 10 wt %, specifically 0.001 to 5 wt %, and more specifically 0.001 to 1 wt %, and in this case, the dispersion may contain a balance of a dispersion medium.

In an exemplary embodiment of the present invention, when the dispersion is spotted in the same region in an amount of 0.001 to 100 µl (25° C., 1 atm) two times or more and specifically two to ten times, it is possible to maintain a distributed loading state of a regular pattern with a more stable structure, and more precise qualitative and quantitative analysis may be performed.

An average thickness of the tungsten ditelluride layer may be appropriately controlled according to the loading amount and loading state of the tungsten ditelluride nanoflake particles, and may be, for example, 0.001 to 500 µm. When this thickness is satisfied, the loading state may be more stably maintained, and more precise qualitative and quantitative analysis may be performed. In addition, a width (horizontal or vertical width) of the tungsten ditelluride layer is not particularly limited because it may be appropriately adjusted according to an analysis/measurement scale, and may be, for example, 0.001 to 10 mm.

As described above, the method of detecting vitamin D in blood using LDI-MS and the apparatus therefor according to the present invention may be used for qualitative or quantitative analysis of vitamin D present in blood.

The detection method and apparatus according to the present invention may be used as various applicable methods. As an example, the present invention may be provided as an LDI-MS sample loading kit including an LDI-MS sample loading array, and may be provided as a laser desorption/ionization mass spectrometer including an LDI-MS sample loading array.

As described above, when the LDI-MS sample loading array according to the present invention is used, quantitative analysis may be more precise in comparison to the case of analysis means according to the related art, such as LC-MS/MS. This means that very precise quantitative analysis may be performed by using tungsten ditelluride in the present invention. In particular, in the present invention, the measurement is simpler and faster, and quantitative analysis may be more precise, compared to LC-MS/MS, as there is no limitation of LC-MS/MS, which takes a lot of time in the measurement process.

Hereinafter, the present invention will be described in detail with reference to Production Examples and Examples. However, these Production Examples and Examples are intended to describe the present invention in more detail, and the scope of the present invention is not limited by the following Examples.

Example 1

<Production of LDI-MS Sample Loading Array>

$WTe_2$ crystals with a purity of 99.9995% were sonicated to prepare a tungsten ditelluride dispersion in which 100 mg of tungsten ditelluride nanoflake particles ($WTe_2$ flakes, 2D semiconductors) formed in a single layer to several layers and having an average thickness of 1 nm and an average long axis of 10 nm to 10 µm were dispersed in 1 kg of isopropanol. Subsequently, a chip-based LDI-MS array was prepared using the tungsten ditelluride dispersion. Specifically, the tungsten ditelluride dispersion was spotted on a stainless steel wafer having a thickness of 1 mm five times using a micro-droplet dispenser, and the tungsten ditelluride dispersion was sufficiently dried, thereby producing an LDI-MS sample loading array including a tungsten ditelluride layer formed by uniformly depositing the tungsten ditelluride nanoflake particles on the wafer. At this time, a volume of the tungsten ditelluride dispersion per spotting was adjusted to 0.1 µl.

<Evaluation of Quantitative Analysis of Vitamin D Using LDI-MS Array>

It is difficult to directly determine a concentration of a drug due to an unpredictable ionization behavior of molecules. Therefore, it is required to add an internal standard having desorption/ionization properties similar to those of vitamin D. That is, in order to quantify a content of the vitamin D in clinical samples, mass spectrometry of vitamin D was performed by a molecular weight difference using an internal standard having physicochemical properties (ionization properties, solubility, and the like) similar to those of a target molecule. The results are illustrated in FIGS. 2 to 7.

1. Sample Preparation

In order to extract 25-hydroxyvitamin $D_3$ in a steroid lipid molecular structure in a serum state, liquid-liquid extraction (LLE) was primarily performed using hexane as a non-polar solvent. Non-steroid lipids were also extracted from a nucleic acid layer. Therefore, 25-hydroxyvitamin $D_3$ was selectively extracted by drying the nucleic acid layer and dissolving the nucleic acid layer using acetonitrile.

In order to prepare a reagent for a calibration curve, 10 µl of each of a vitamin and an internal standard was spiked into 100 µl of human serum, and the serum was vortexed for 5 seconds. Then, the serum was incubated at room temperature for 30 minutes, and then, 200 µl of methanol was slowly added while the serum was lightly vortexed. The serum was incubated at room temperature for 10 minutes, 600 µl of hexane and 150 µl of a sodium carbonate aqueous solution at a concentration of 20 g/l were added, and then, the serum was lightly vortexed. Subsequently, the serum was centrifuged at 2,000 rpm for 10 minutes and then stored at −70° C. for 30 minutes. An organic solvent layer that was a supernatant was separated from an aqueous layer to transfer to a clean tuber, 500 µl of hexane was added again to the aqueous layer that was a lower layer, centrifugation and freezing were repeated under the same conditions, and extraction was performed by adding a sample. In addition, the organic solvent layer transferred separately was dried with nitrogen gas, 100 µl of acetonitrile was added, and centrifugation was performed at 10,000 rpm for 10 minutes. After the centrifugation, finally, only the acetonitrile layer was separated, drying was performed again, and a derivatization reaction was performed. For the clinical sample, an internal standard was spiked into 100 µl of serum at the same concentration, and then, a pretreatment was performed.

By this method, a derivatized material was introduced into the sample pretreated through liquid-liquid extraction, and a reaction was performed at room temperature for 30 minutes. In addition, C18 solid phase extraction (SPE) was performed to remove the matrix present in the serum extract, and then, the serum extract was loaded on the LDI-MS sample loading array produced in Example 1.

2. Mass Spectrometry

In the method of standard addition using an internal standard, after an internal standard whose concentration and amount are known is added to a sample to be analyzed, a standard solution of the measurement material is added to the sample step by step, and a concentration is determined by a calibration curve obtained by measuring a ratio of 25OH-vitamin $D_3$ to 25OH-vitamin $D_3$-$d_3$ used as an internal standard. A recovery rate in the entire pretreatment process may be corrected from the internal standard whose concentration and content are accurately determined, and the method of standard addition is a method of increasing measurement accuracy by correcting a measurement bias due to a matrix effect according to the medium of the sample. It is preferable to select an element that has a physical and chemical behavior similar to that of a target element to be analyzed and does not exist in the sample as the internal standard.

Starting from a 25OH-vitamin $D_3$-$d_3$ solution as an internal standard, the solution was gravimetrically diluted to prepare a 25OH-vitamin $D_3$-$d_3$ working standard solution (ISTD solution), and a correct amount of the ISTD solution was added to a certain amount of sample. In addition, in order for the method of standard addition, starting from a 25OH-vitamin $D_3$ solution, the solution was gravimetrically diluted to prepare standard addition working standard solutions (SA working solutions) at different concentrations, and a correct amount of the SA working solution was added to each sample in which the internal standard was added in response to each concentration.

For the measurement of the content of 25OH-vitamin $D_3$ in the blood sample using LDI-MS, the pretreated sample was dropped and loaded on the LDI-MS sample loading array five times, and analysis was performed. In the present analysis, a measurement was performed using a matrix assisted laser desorption/ionization (MALDI) system of SynapG2 equipment manufactured by Waters Corporation. At this time, a Nd:YAG laser of 355 nm was used as an ionization source, and a laser power of 350 (a.u.) was used. The measurement was performed by fixing trap collision energy of the analyst to 6.0 V and fixing transfer collision energy to 2.0 V. A quadrupole profile was measured by increasing the sensitivity by applying a manual profile increasing the sensitivity of the analysis mass range. The mixed standard solution sample and the sample to be analyzed were repeatedly measured a certain number of times until the end. When the number of samples was large, the mixed standard solution samples were sampled at appropriate intervals between the samples, and analysis was performed.

3. Experimental Results

FIGS. 2 to 6 illustrate laser desorption/ionization mass spectrometry spectra (LDI-MS for 25OH-vitamin $D_3$) obtained by measuring vitamin $D_3$ in plasma using the LDI-MS sample loading array of Example 1.

As illustrated in FIGS. 2 to 6, it can be confirmed that the concentrations of the 25OH-vitamin $D_3$ sample in plasma are observed as the spectra when performing the measurement using LDI-MS until the concentrations reached up to 16 pmol/µl, 1.6 pmol/µl, 0.16 pmol/µl, 0.016 pmol/µl, and 0.008 pmol/µl.

Figure 1:
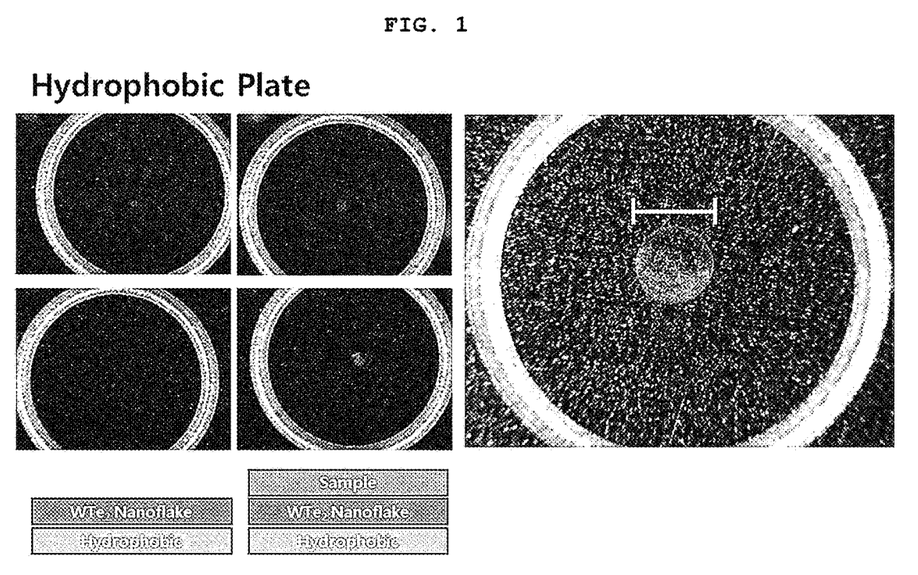
FIG. 1 is an image (top) showing a laser desorption/ionization mass spectrometry (LDI-MS) sample loading array according to the present invention and an image (bottom) showing a stacked structure.
Figure 2:
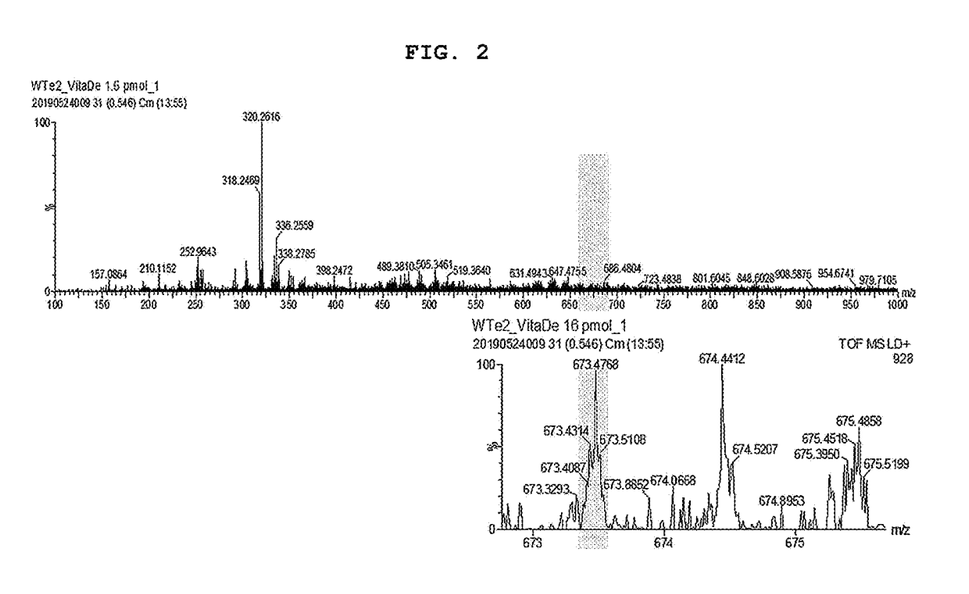
FIGS. 2 to 6 illustrate laser desorption/ionization mass spectrometry spectra (LDI-MS for 25OH-vitamin $D_3$ $WTe_2$) obtained by measuring 25OH-vitamin $D_3$ in plasma using an LDI-MS sample loading array of Example 1.
Figure 3:
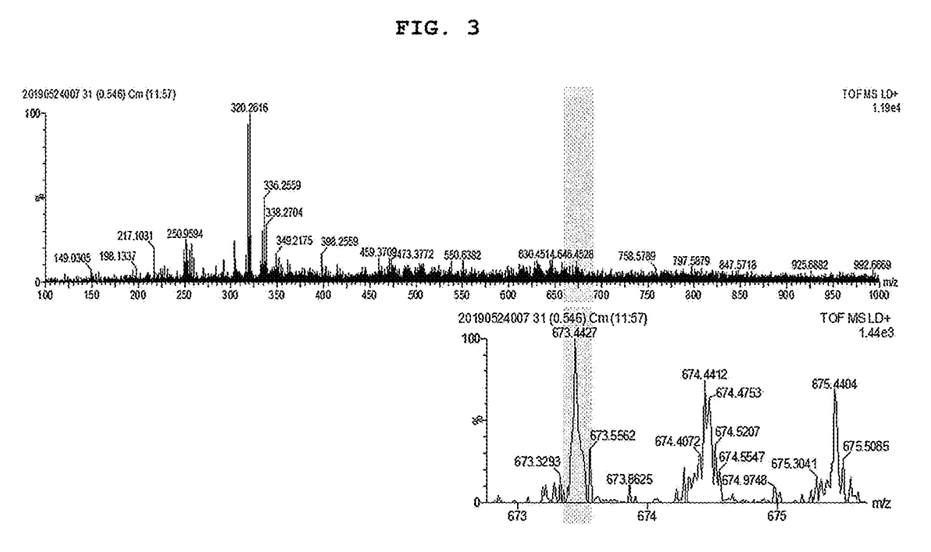
Figure 4:
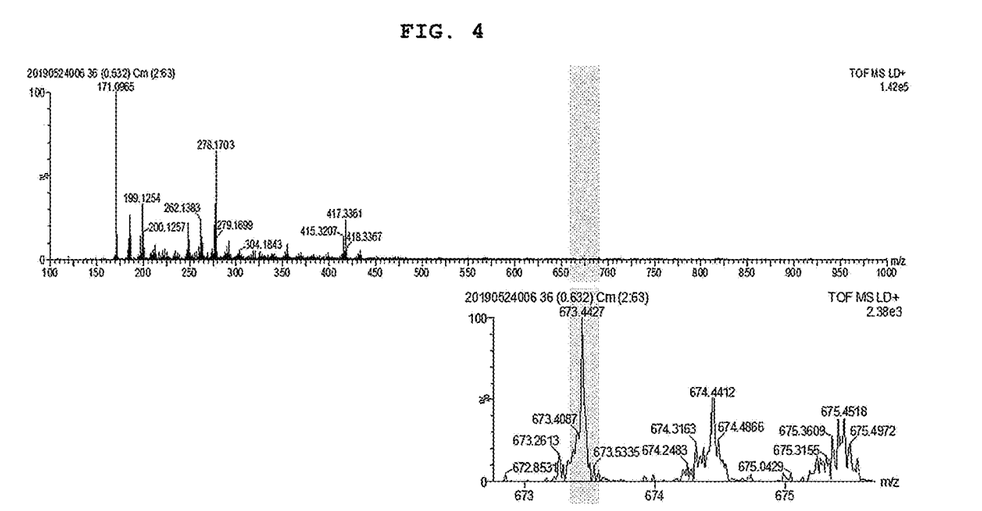
Figure 5:
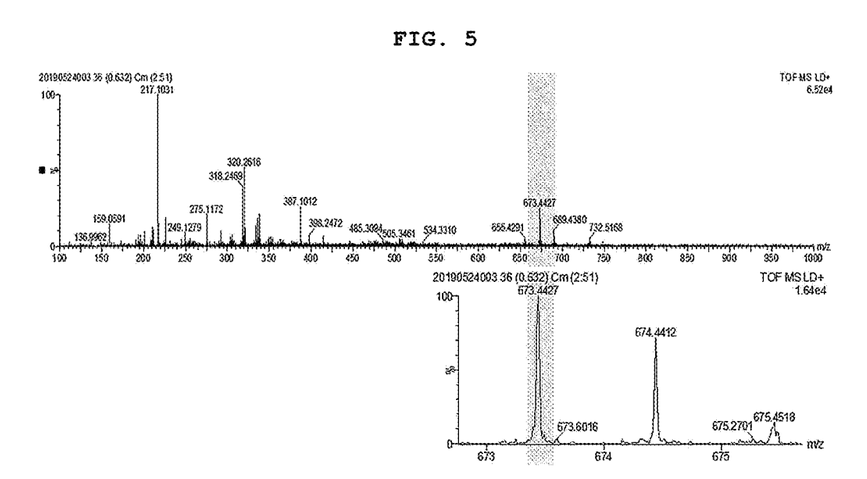
Figure 6:
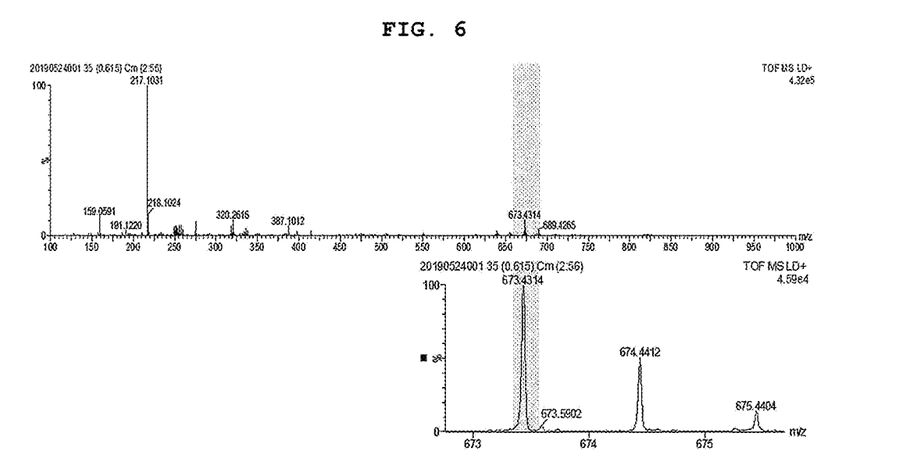
Figure 7:
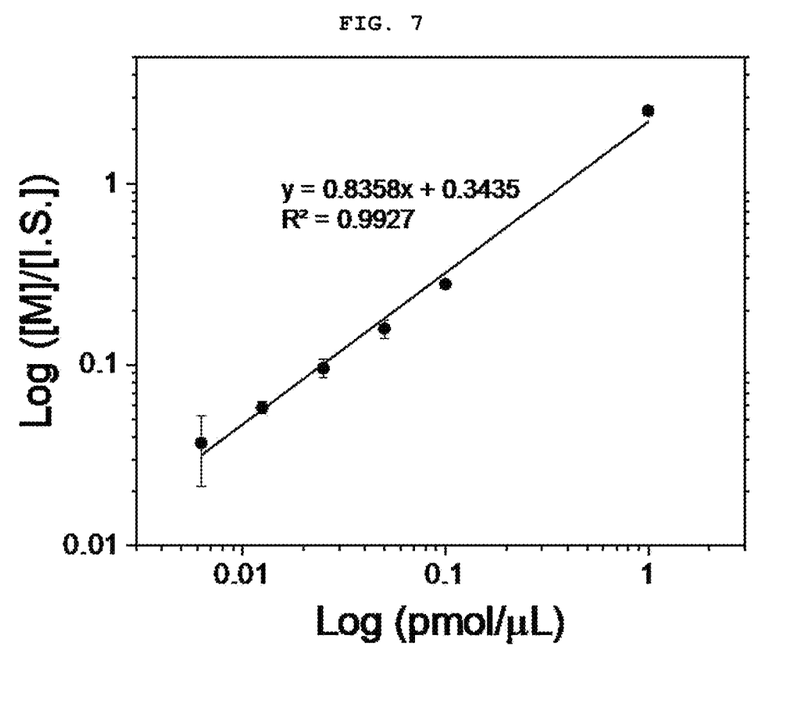
FIG. 7 is a graph showing the laser desorption/ionization mass spectrometry spectrum obtained by measuring 25OH-vitamin $D_3$ in plasma using the LDI-MS sample loading array of Example 1 as a calibration curve.

FIG. 7 is a graph showing the laser desorption/ionization mass spectrometry spectrum obtained by measuring vitamin $D_3$ in plasma using the LDI-MS sample loading array of Example 1 as a calibration curve. It can be confirmed that the calibration curve is linear in the entire concentration range including the clinical effective concentration range, and the $R^2$ value is 0.9927.

Therefore, it can be appreciated that the measurement using WS2 LDI-MS according to the present invention may be significantly efficient in cost and time as a platform with simple analysis and a simple production process in comparison to the case using LC-MS/MS, may have the advantage of immediate and real-time quantitative analysis, and may replace LC-MS/MS because quantitative analysis as precise as or higher than LC-MS/MS may be performed.

As set forth above, the method of detecting vitamin D in blood using LDI-MS and the apparatus therefor according to the present invention are not complicated in the measurement, do not require a number of measurement steps, and allow for easy measurement and collection of results in real time with a quick analysis.

The method of detecting vitamin D in blood using LDI-MS and the apparatus therefor according to the present invention may implement precise analysis even at a lower concentration of the sample, such that sensitivity and precision are excellent, various subtypes of vitamin D may be simultaneously detected, a throughput is high, and structural analysis and quantitative analysis of vitamin D that has undergone a metabolic process in blood may be accurately performed without a matrix interference.

Although the effects are not explicitly mentioned in the present invention, the effects described in the specification anticipated by the technical features of the present invention and the inherent effects thereof are treated as described in the specification of the present invention.

What is claimed is:

1. A method of detecting vitamin D in blood using laser desorption/ionization mass spectrometry (LDI-MS), the method comprising:
    adding an internal standard to a sample comprising blood;
    loading the sample on a tungsten ditelluride layer of an LDI-MS sample loading array including a substrate layer and the tungsten ditelluride layer stacked on the substrate layer;
    acquiring an LDI-MS spectrum of the sample; and
    setting a ratio of a peak intensity of the internal standard to a peak intensity of vitamin D identified in the LDI-MS spectrum on a y-axis and setting a concentration of vitamin D in the sample on an x-axis to obtain a calibration curve.

2. The method of claim 1, wherein the tungsten ditelluride layer includes a plurality of tungsten ditelluride nanoflake particles in contact with the substrate layer.

3. The method of claim 2, wherein an average thickness of the tungsten ditelluride nanoflake particles is 2 to 15 nm.

4. The method of claim 2, wherein the tungsten ditelluride nanoflake particles in the tungsten ditelluride layer is present in an amount of 0.0001 to 100 mg/cm$^2$ per unit area.

5. The method of claim 2, wherein the tungsten ditelluride layer is produced by spotting a solution in which tungsten ditelluride nanoflake particles are dispersed on the substrate layer and then evaporating a dispersion medium.

6. The method of claim 5, wherein the tungsten ditelluride nanoflake particles in the solution are included in an amount of 0.001 to 10 wt %.

7. The method of claim 6, wherein the solution is spotted in the same region in an amount of 0.001 to 100 µl (25° C., 1 atm) two times or more.

8. The method of claim 1, a coefficient of determination ($R^2$) in the calibration curve is 0.9 or more.

9. The method of claim 1, wherein an average thickness of the tungsten ditelluride layer is 0.001 to 500 µm.

10. The method of claim 1, wherein the substrate layer includes one or two or more selected from aluminum, copper, iron, nickel, zinc, chromium, silver, and silicon.

* * * * *